United States Patent [19]

Ryan

[11] Plant 4,258

[45] June 6, 1978

[54] IMPATIENS PLANT MAYA

[76] Inventor: John J. Ryan, 39877 Sundale Dr., Fremont, Calif. 94538

[21] Appl. No.: 782,284

[22] Filed: Mar. 28, 1977

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Maya, and discovered by me in commercial greenhouses in Fremont, Calif. Maya is closest in characteristics to Mikkel Red Magic particularly characterized by its excellent floriferousness; good breaking action making a full basket and giving good cutting production; red-green foliage like Mikkel Red Magic; fast growth habit; a light red-orange flower; and the ability to withstand adverse conditions.

1 Drawing Figure

BACKGROUND OF THE INVENTION

The present new variety (seedling 76-13-1) was discovered by me in commercial greenhouses in Fremont, Calif. as a result of the cross pollination of unpatented pistil parent 75-7 and unpatented pollen parent 75-8.

Asexual reproduction of my new cultivar by terminal or stem cuttings grown in 6" pots in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Maya is closest in characteristics to Mikkel Red Magic.

The following outstanding characteristics of Maya distinguish it from Mikkel Red Magic:

1. Floriferousness — although Red Magic produces many flowers, Maya produces more.
2. Breaks very well, making a good basket. Red Magic has too stiff a stem and too long an internode to make a good basket.
3. The red-green foliage is very similar to Red Magic.
4. Growth rate is equal to or greater than Red Magic.
5. Flower is light red-orange, unlike the rose-red of Red Magic.
6. Flower is about half the size of Red Magic.
7. Stands up, as well as, if not better than Red Magic to adverse conditions or neglect.

DESCRIPTION OF THE PHOTOGRAPH

The accompanying colored photograph illustrates the overall appearance of the cultivar Maya showing the colors slightly darker than the plant. However, under low light and cool temperatures the flower color darkens. Under high light the foliage darkens and the flower becomes more orange.

The following detailed description of Maya is based on observations made of the new cultivar on Jan. 13, 1977.

PLANT

Name: Maya.
Origin: Seedling 76-13-1 of the cross pollination of unpatented pistil parent 75-7 and unpatented pollen parent 75-8.
Form: Upright with spreading tendency.
Height to flowering: 15 to 30 cm.
Growth: Moderate to fast.
Type of cutting: Terminal or stem.
Rooting time: Typical, 10–14 days.
Rooting habit: Fast, dentritic.

FOLIAGE

Arrangement: Lower leaves (usually only one set) opposite; upper foliage of any shoot whorls of 3–5, mostly 3–4.
Shape: Oblanceolate.
Tip: Broadly acuminate.
Base: Attenuate.
Margin: Ciliate at base to serrulate at tip.
Venation: Pinnate.
Size: Blade and petiole 12 to 15 cm.; length of blade 10 to 11 cm.; width at widest point of blade — 4 cm.
Surface:
*Smoothness.*—Rare crinkling.
*Texture.*—Glabrous, typically waxy.
Variegation: None.
Color:
*Petiole.*—Bottom 46A, top 48B.
*Veins.*—Bottom 46A, top 48B.
*Leaf.*—a. Upper 147A, as close as possible for red-green color mix. b. Lower 47A but grayed by red sheen.

STEM

Color: 47A.
Internode:
*Length.*—Moderate.
*Size.*—Moderate.
Node expanded (relative to internode): Slightly.
Breaking action: Very good.

FLOWER

Form: Typical.
Borne: End of branches; terminal.

Blooming habit:

*Relative number.*—Very good to profuse.

*Time to flowering.*—Short to moderate.

*Longevity.*—Typical (3–5 days), heavily dependent on temperature.

Size of mature flower: First flower on a plant may be small.

*Length.*—5.0 cm.

*Width.*—4.5 cm.

*Spur.*—6.0 cm.

Color: Lightens under high light.

*Eye.*—63A.

| | |
|---|---|
| 1. Eye: 63A | |
| 2. Middle | 40A |
| 3. Edge | |
| 4. Pedicel: 195B | |

*Pedicel.*—195B.

REPRODUCTIVE ORGANS

Stamen:

| | |
|---|---|
| 1. Anthers | typical, fused hood over pistil |
| 2. Filaments | |

-continued

| |
|---|
| 3. Pollen |
| a. Color: 158C |
| b. Abundance: typical, plenty |

*Pollen.*—a. Color: 158C. b. Abundance: typical, plenty.

Pistils:

| | |
|---|---|
| 1. Style | typical |
| 2. Ovaries | |

OTHER CHARACTERISTICS

Disease: Maya is less susceptible than other varieties to most soft rots.

I claim:

1. A new and distinct form of Impatiens plant as described and illustrated known by the cultivar name Maya and particularly characterized by its excellent floriferousness; good breaking action; making a full basket; giving good cutting production; red-green foliage like Mikkel Red Magic: fast growth habit; a light red-orange flower; and the ability to withstand adverse conditions.

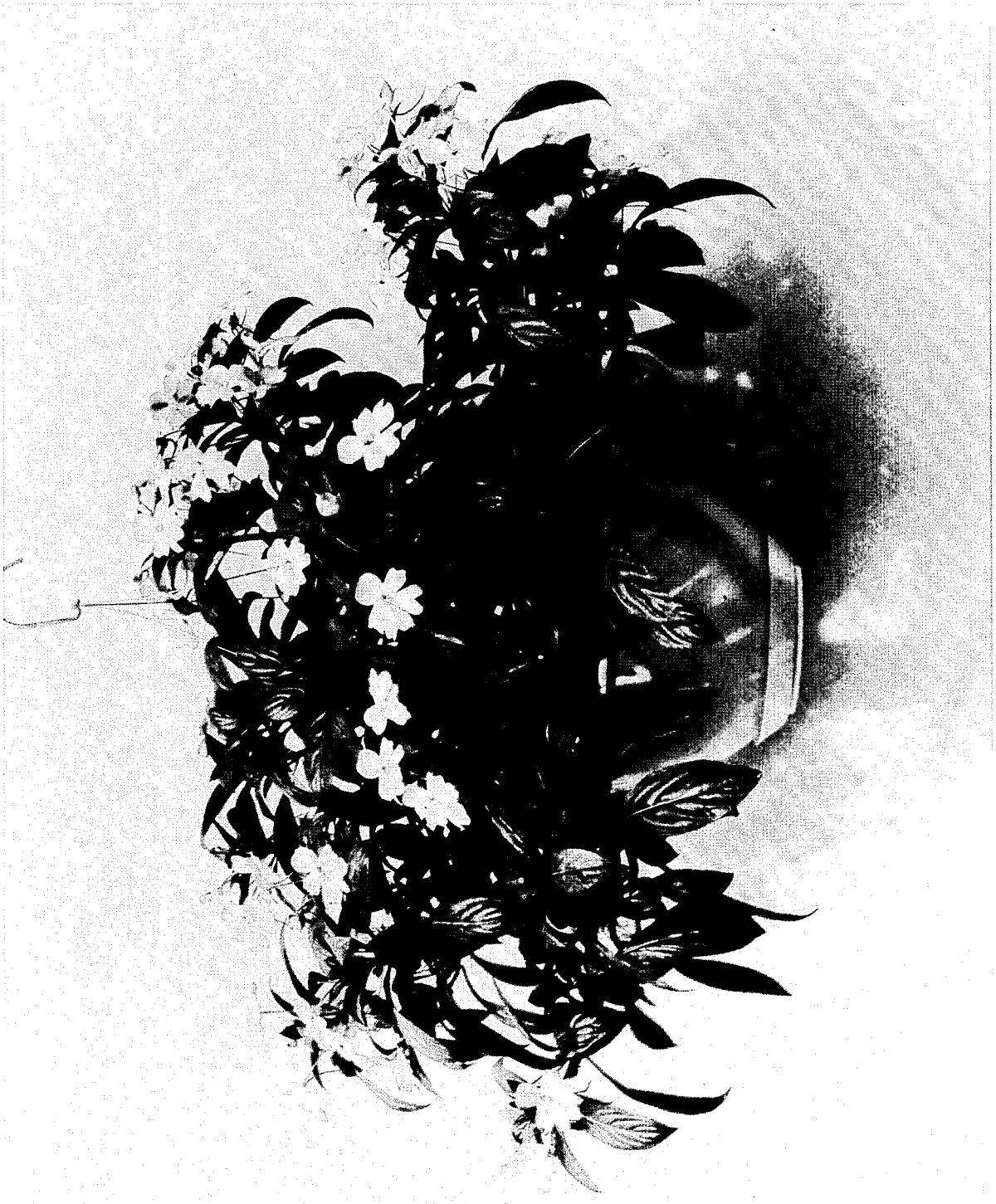

* * * * *